United States Patent [19]

Arney et al.

[11] Patent Number: 5,047,045
[45] Date of Patent: Sep. 10, 1991

[54] MULTI-SECTION COAXIAL ANGIOPLASTY CATHETER

[75] Inventors: Michelle M. Arney; Matthew M. Burns, both of Minneapolis, Minn.

[73] Assignee: Scimed Life Systems, Inc., Maple Grove, Minn.

[21] Appl. No.: 433,712

[22] Filed: Nov. 13, 1989

Related U.S. Application Data

[63] Continuation-in-part of Ser. No. 337,319, Apr. 13, 1989, abandoned.

[51] Int. Cl.$^5$ ............................................. A61M 25/00
[52] U.S. Cl. ...................................... 606/194; 604/96; 604/280
[58] Field of Search ................. 604/96, 102, 103, 264, 604/280, 281, 282; 606/191–194

[56] References Cited

U.S. PATENT DOCUMENTS

| | | | |
|---|---|---|---|
| 4,323,071 | 4/1982 | Simpson et al. | |
| 4,456,000 | 6/1984 | Schjeldahl et al. | 604/194 |
| 4,496,345 | 1/1985 | Hasson | 604/103 |
| 4,573,470 | 3/1986 | Samson et al. | 604/96 |
| 4,597,755 | 7/1986 | Samson et al. | 604/96 |
| 4,646,742 | 3/1987 | Packard et al. | 606/194 |
| 4,729,914 | 3/1988 | Kliment et al. | 604/96 |
| 4,762,129 | 8/1988 | Bonzel | 606/194 |
| 4,775,371 | 10/1988 | Mueller, Jr. | |
| 4,798,586 | 1/1989 | Stevens | 604/96 |
| 4,819,751 | 4/1989 | Shimada et al. | 606/196 |
| 4,820,349 | 4/1989 | Saab | 604/96 |
| 4,838,268 | 6/1989 | Keith et al. | |
| 4,846,174 | 7/1989 | Willard et al. | 604/96 |
| 4,877,031 | 10/1989 | Conway et al. | 604/96 |
| 4,896,670 | 1/1990 | Crittenden | 604/96 |
| 4,906,241 | 3/1990 | Noddin et al. | 604/96 |
| 4,921,483 | 5/1990 | Wijaq et al. | 604/96 |
| 4,943,278 | 7/1990 | Euteneur et al. | 604/96 |
| 4,946,466 | 8/1990 | Pinchuk et al. | 604/96 |
| 4,976,690 | 12/1990 | Solar et al. | 606/194 |

FOREIGN PATENT DOCUMENTS

| | | | |
|---|---|---|---|
| 0279958 | 8/1988 | European Pat. Off. | 604/280 |
| 0351687 | 1/1990 | European Pat. Off. | |
| WO86/06285 | 6/1989 | PCT Int'l Appl. | |
| 2130093 | 5/1984 | United Kingdom | 604/264 |

Primary Examiner—Stephen C. Pellegrino
Assistant Examiner—Ralph A. Lewis
Attorney, Agent, or Firm—Kinney & Lange

[57] ABSTRACT

An over-the-wire balloon catheter for use in angioplasty includes a dual lumen shaft formed by a multi-section outer tube with a multi-section inner tube coaxially aligned therein. The outer tube includes a proximal hypotube outer tube section which is connected to a manifold at its proximal end. The outer tube also includes a distal high density polyethylene outer tube section which is attached to the distal end of the proximal outer tube section at an outer tube bonding region. The inner tube has a proximal polyimide inner tube section which extends generally coaxially through the proximal outer tube section. The inner tube also includes a distal high density polyethylene inner tube section which is attached to the distal end of the first inner tube section at an inner tube bonding region. The inner tube bonding region is spaced proximally from the outer tube bonding region, and a balloon is attached to the distal ends of the outer and inner tubes.

23 Claims, 1 Drawing Sheet

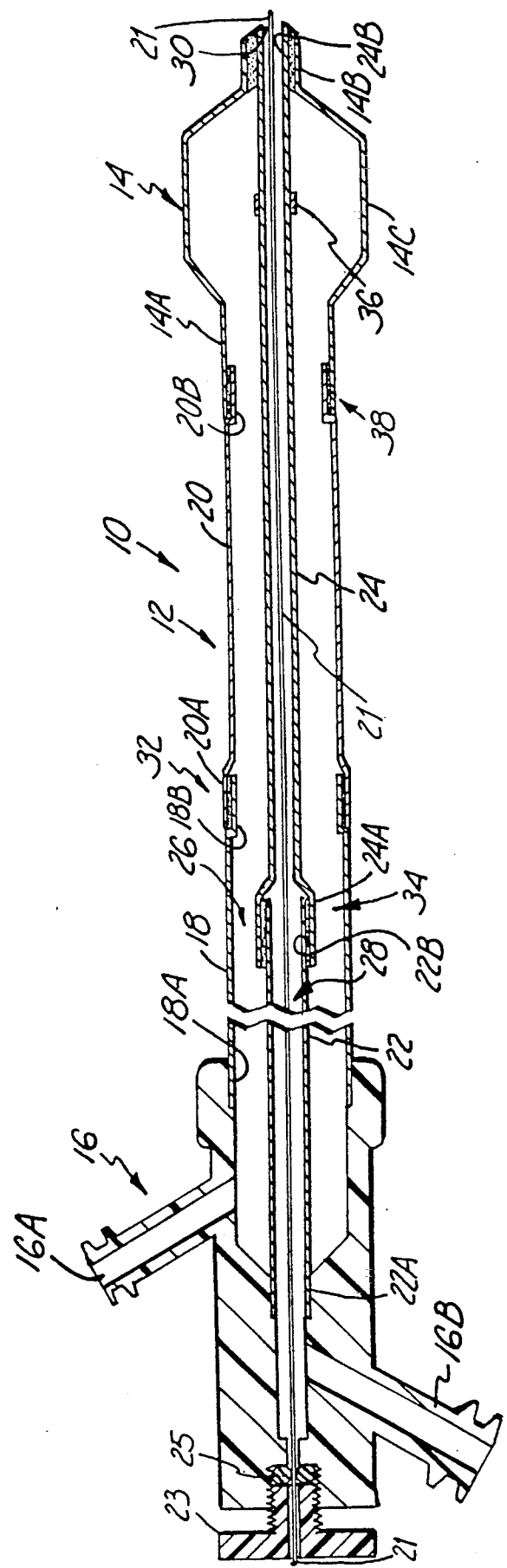

MULTI-SECTION COAXIAL ANGIOPLASTY CATHETER

This application is a continuation-in-part of Applicant's co-pending application Ser. No. 07/337,319, filed Apr. 13, 1989, now abandoned which is incorporated by reference herein.

BACKGROUND OF THE INVENTION

The present invention relates to the field of angioplasty. In particular, the present invention relates to a dilatation balloon catheter of the "over-the-wire" type.

Angioplasty has gained wide acceptance in recent years as an efficient and effective method for treating types of vascular disease. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Typically, a hollow guide catheter is used in guiding the dilatation catheter through the vascular system to a position near the stenosis (e.g., to the aortic arch). Using fluoroscopy, the physician guides the dilatation catheter the remaining distance through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

There has been a continuing effort to reduce the profile and shaft size of the dilatation catheter so that the catheter not only can reach but also can cross a very tight stenosis. A successful dilatation catheter must also be sufficiently flexible to pass through tight curvatures, especially in the coronary arteries. A further critical requirement for a successful dilatation catheter is its "pushability". This involves the transmission of longitudinal force along the catheter from its proximal end to its distal end so that a physician can push the catheter through the vascular system and the stenosis. In addition, a rotation ("twist" or "torque") of the catheter shaft at its proximal end should be evenly translated by the catheter to its distal end so that torque does not build up in the catheter which might cause it to rapidly unwind at its distal end during use.

Two commonly used types of dilatation catheters are referred to as "over-the-wire" catheters and "non-over-the-wire" catheters. An over-the-wire catheter is one in which a separate guide wire lumen (sometimes called a "thru lumen") is provided so that a guide wire can be used to establish the path through the stenosis. The dilatation catheter can then be advanced over the guide wire until the balloon is positioned within the stenosis. One problem with the over-the-wire catheter is the requirement of a larger profile and a generally larger outer diameter along its entire length in order to allow for a separate guide wire lumen.

A non-over-the-wire catheter acts as its own guide wire, and thus there is no need for a separate guide wire lumen. One advantage of a non-over-the-wire catheter is its potential for a reduced outer diameter along its main shaft since a guide wire lumen is not required. However, one disadvantage is the inability to maintain the position of a guide wire within the vascular system when removing the catheter and exchanging it for one of a smaller (or larger) balloon diameter. Thus, to accomplish an exchange with the non-over-the-wire catheter, the path to the stenosis must be reestablished when replacing the catheter with one having a different balloon diameter.

A recent innovation in non-over-the-wire catheters is to employ a thin wall metal tube, such as an hypodermic tubing, for at least a proximal portion of the main shaft of the catheter. Using a long and narrow thin wall metal tube provides enhanced pushability for such catheters. Examples of non-over-the-wire catheters that use a metal tube shaft are seen in Keith et al. U.S. Pat. No. 4,838,268, issued June 13, 1989, and in PCT Publication No. WO86/06285, published Nov. 6, 1989. Flexibility is not as great a concern in the proximal portion of the catheter shaft, and particularly that portion thereof which is passing through the guide catheter. It is the distal portion of the catheter shaft which must negotiate the tortuous portions of the arteries in the vascular system in order to reach the lesion. Of course, reducing the profile and shaft size of a catheter is a continuing concern, and the use of thin wall metal tubing also assists in attaining these ends.

In over-the-wire catheters, the factors of transmit torque have not been quite as critical since the catheter is typically tracking over an existing guide wire through the vascular system. Shaft materials for over-the-wire catheters have typically consisted of polymer-based materials such as polyethylene. With the continuing emphasis on shaft size reduction and the emergence of small diameter guide wires and small diameter guide catheters, however, the reduction in shaft sizes for polymer-based shafts of over-the-wire catheters has diminished the pushability of such shafts. There is thus a need for the development of an over-the-wire catheter with a smaller diameter shaft that exhibits good characteristics of pushability, and the requisite flexibility at the distal end of the catheter to negotiate the coronary arteries.

SUMMARY OF THE INVENTION

The present invention is an over-the-wire dilatation catheter which uses a multi-section outer tube and a multi-section inner tube to achieve a very small outer diameter, and which exhibits exceptional pushability by use of a thin wall metal tube as the proximal section of its outer tube, in combination with a desired degree of flexibility at the distal end of the catheter.

The present invention makes use of a multisection outer tube and a multi-section inner tube with a balloon attached to the distal ends of the inner and outer tubes. An inflation lumen is formed between the outer wall of the inner tube and the inner wall of the outer tube. A guide wire or thru lumen extends through the interior of the inner tube.

The inner tube has a proximal thin wall polymer tube section and a distal thin wall polymer tube section. The proximal and distal sections of the inner tube are connected together at an inner tube bonding region and as such, define the guide wire lumen therein. The distal inner tube section is more flexible than the proximal inner tube section. The outer tube has a proximal thin wall metal tube section and a distal thin wall polymer tube section. The proximal and distal sections of the outer tube are connected together at an outer tube bonding region which is spaced distally from the inner tube bonding region, and the distal outer tube section is more flexible than the proximal outer tube section. A balloon has a proximal portion thereof connected to a distal end of the distal outer tube section and a distal portion thereof connected to a distal end of the distal inner tube section.

In preferred embodiments of the present invention, the proximal outer tube section is a stainless steel hypotube, the proximal inner tube section is a polyimide tube, the distal inner tube section is a high density polyethylene tube and the distal outer tube section is a high density polyethylene tube. Preferably, the outer tube bonding region is spaced approximately two centimeters distally from the inner tube bonding region.

BRIEF DESCRIPTION OF THE DRAWINGS

The FIGURE is a sectional view of the dilatation balloon catheter of the present invention. The FIGURE is not to scale, and some parts are exaggerated for clarity.

DETAILED DESCRIPTION

Dilatation balloon catheter 10 shown in the FIGURE is a coaxial dual lumen dilatation catheter which has a very small outer diameter. Dilatation balloon catheter 10 is formed by a multi-lumen shaft 12 which has an inflatable balloon 14 mounted at its distal end and a manifold 16 mounted at its proximal end.

Shaft 12 includes a multi-section outer tube (formed by proximal outer tube section 18 and distal outer tube section 20) and a multi-section inner tube (formed by proximal inner tube section 22 and distal inner tube section 24). Inflation lumen 26 is defined between the outer walls of inner tube sections 22 and 24 and the inner walls of outer tube sections 18 and 20. Inflation lumen 26 extends from manifold 16 to the interior of balloon 14. Guide wire (or thru) lumen 28 extends through the interior of inner tube sections 22 and 24 from manifold 16 to distal opening 30 at the distal end of catheter 10, for reception of a guide wire 21. The guide wire 21 extends proximally through manifold 16 and through a thumbscrew 23 threadably mounted thereon. The guide wire 21 can be immobilized against longitudinal movement relative to manifold 16 by tightening of thumbscrew 23. This compresses an O-ring 25 between the thumbscrew 23 and manifold 16, which deforms radially inwardly about guide wire 21. In addition to securing guide wire 21 in place, the deformation of the O-ring 25 also effectively seals off the proximal end of guide wire lumen 28 in manifold 16.

Proximal outer tube section 18 has its proximal end 18A connected to manifold 16 and its distal end 18B bonded to proximal end 20A of distal outer tube section 20 at an outer tube bonding region 32. Manifold 16 has an inflation port 16A which is in fluid communication with inflation lumen 26. An inflation device (not shown) is connected to inflation port 16A to introduce balloon inflation fluid (e.g., a 50/50 solution of radiopaque dye and saline) into inflation lumen 26. Distal end 20B of distal outer tube section 20 is bonded to proximal waist section 14A of balloon 14.

Inner tube section 22 has a proximal end 22A which extends proximally beyond proximal end 18A of outer tube section 18 and is bonded to manifold 16 proximally of proximal end 18A of the proximal outer tube section 18. Manifold 16 has a second port 16B which is in fluid communication with guide wire lumen 28. A fluid source (not shown) is connected to second port 16B to introduce fluid (e.g., saline solution) into guide wire lumen 28 prior to use of catheter 10 to purge air from the guide wire lumen 28. At its distal end 22B, inner tube section 22 is connected to proximal end 24A of inner tube section 24 at an inner tube bonding region 34. Inner tube bonding region 34 is spaced proximally of outer tube bonding region 32. Distal end 24B of inner tube section 24 is bonded to distal section 14B of balloon 14.

Balloon 14 has an intermediate, inflatable section 14C located between proximal segment 14A and distal segment 14B. The interior of balloon 14 is in fluid communication with inflation lumen 26. In the FIGURE, balloon 14 is shown in its inflated condition. Preferably, balloon 14 is formed from a polyimide or polyolefin material.

In order to achieve a very small outer diameter, while retaining the necessary pushability and flexibility characteristics and the ability to handle high inflation pressures, tube sections 18, 20, 22 and 24 are formed from thin wall, high strength tubing sections. In a preferred embodiment, the maximum outer diameter of the outer tube of shaft 12 is 0.0405 inch. Preferably, proximal outer tube section 18 is a stainless steel hypotube. The term "thin wall" as used in this application means a wall thickness of equal to or less than 0.0034 inch. Stainless steel hypotube is desireable because it offers the advantages of a thin wall construction with the necessary strength to achieve the needed pushability, high burst pressure rating and small shaft diameter.

In a preferred embodiment, proximal inner tube section 22 is a polyimide tube having a thin wall construction. In use, the proximal inner tube section 22 is within the stiffer proximal outer tube section 18 (and the guide catheter), and thus it also is not subject to extreme bending. Movement of the guide wire 21 through the proximal inner tube section 22 is, therefore, relatively good even if the proximal inner tube section 22 is not provided with a lubricious inner surface. Should lubrication for the inner proximal tube section 22 be desired, the inner surface thereof is preferably composed of a lubricious material. Hydrophobic materials such as tetrafluoroethylene or a polyimide-polytetrafluoroethylene composite have been found to be desireable because they provide for a low friction inner surface that allows free guide wire movement (axial and torsional) in and thru guide wire lumen 28, despite very small clearances. In a further embodiment, such desired lubricity can be obtained by use of a hydrophilic coating material such as a polyacrylamide polyurethane substrate.

Distal outer tube section 20, in a preferred embodiment, is formed from a thin wall, high density polyethylene. Such high density polyethylene tubing has greater flexibility than the stainless steel hypotube which forms proximal outer tube section 18. This greater flexibility allows the distal end of catheter 10 to be guided through the tortuous passages of the coronary artery. Less flexibility is required for proximal outer tube section 18, which in use, extends only within the confines of the guide catheter. The guide catheter extends through the less tortuous portion of the vascular system, so flexibility of the proximal portion of the outer tube is not so important, while pushability and tube diameter reduction are still important.

The material selected for distal outer tube section 20 must have thin walls together with the appropriate level of flexibility and a relatively high burst pressure. This distal section must negotiate the twists and turns of the coronary artery. Thin wall, high density polyethylene tubing has been found to have these desired characteristics.

A lubricious outer surface is desired for both sections of the outer tube. The use of a high density polyethylene tube for distal outer tube section 20 attains this end, since polyethylene is an inherently lubricious material. Thus, in a preferred embodiment, distal outer tube section 20 is high density polyethylene that is not coated or treated with an outer surface lubricant (although in other preferred embodiments a coating may be applied). For a stainless steel hypotube, a preferred lubricious coating is a hydrophobic material such as a polytetrafluoroethylene. In a further embodiment, the desired lubricity is attained by use of a hydrophilic material such as a polyacrylamide polyurethane substrate.

Distal inner tube section 24 is a thin wall, high density polyethylene tube which, as mentioned above, is a relatively lubricious material and therefore needs no lubricant treatment on its inner surface. In one preferred embodiment, however, a hydrophobic lubricious material, such as a polydimethylsiloxane, is provided on the inner surface of distal inner tube section 24. Alternatively, the desired lubricity on the inner surface of distal inner tube section 24 is attained by use of a hydrophilic coating material such as a polyacrylamide polyurethane substrate (if the distal outer tube section 20 were provided with a lubricious coating, these materials would suffice).

The material selected for inner tube sections 22 and 24 must have sufficient strength, even in a thin wall construction, to resist collapse when fluid pressure is applied through inflation lumen 26 to the interior of balloon 14. In the configurations described herein, both polyimide tubing and high density polyethylene tubing offer sufficient strength against collapse with the fluid pressures typically used to inflate balloon 14. In order to maintain a low profile, yet allow catheter 10 to be useable with such small guide wires as 0.014 inch in diameter, the inner tube sections preferably have an inner diameter of about 0.016 inch to about 0.019 inch.

As mentioned above, the inner tube bonding region 34 is spaced proximally of outer tube bonding region 32. The preferable bonding technique for securing the proximal inner tube 22 and distal inner tube 24 is an overlapped arrangement, wherein an end segment of proximal end 24A of distal inner tube 24 is flared outwardly, so that it fits over distal end 22B of proximal inner tube 22. A suitable adhesive bond is then provided therebetween to secure the inner tube sections together to define inner tube bonding region 34. This creates a smooth inner surface transition from one inner tube section to the other, so that movement of a guide wire therethrough will not be inhibited.

Outer tube bonding region 32 is similarly formed. An end segment of proximal end 20A of distal outer tube 20 is flared outwardly. In addition, an end segment of distal end 18B of proximal outer tube 18 is reduced or necked down to a smaller outer diameter. Reduced distal end 18B is then received within enlarged proximal end 20A, and a suitable adhesive bond is provided therebetween to define outer tube bonding region 32. This arrangement creates a smooth outer surface transition from one outer tube to the other.

The effective thicknesses of the walls of the inner and outer tubes are thus enlarged at the bonding regions 32 and 34. Accordingly, the bonding regions are spaced apart, with the inner tube bonding region 34 proximal of the outer tube bonding region 32, so that the flow of inflation fluid through inflation lumen 26 is not inhibited. Further, the inner tube bonding region 34 is positioned proximally of outer tube bonding region 32 and distal end 18B of proximal hypotube outer tube section 18 to protect inner proximal tube 22 and inner tube bonding region 34 from undue bending (the hypotube proximal outer tube section 18 is stiffer than the high density polyethylene distal outer tube section 20). The polyimide proximal inner tube section 22 is, in the preferred embodiment, too stiff to be effective in the distal (flexible) portion of the catheter 10. Accordingly, the polyimide proximal inner tube is maintained entirely within the hypotube proximal outer tube 18. A polyimide tube with the necessary inner diameter to accommodate a 0.014 inch diameter guide wire could damage the polyethylene outer tube or kink if it were in the distal portion of the catheter subject to extensive flexing.

In the preferred embodiment of the present invention seen in the FIGURE, one or more radiopaque markers 36 are provided on the distal inner tube section 24, preferably within the area bounded by the balloon 14. Such markers are provided to aid in inserting and locating the catheter by fluoroscopy in the patient's vascular system during angioplasty.

A preferred embodiment of the multi-section coaxial angioplasty catheter of the present invention is illustrated by the following example. Proximal outer tube section 18 is a stainless steel hypotube having an inner diameter of about 0.0334 inch and an outer diameter of about 0.0374 inch. The hypotube wall thickness is about 0.002 inch. A black polytetraflouroethylene outer surface coating (for added lubricity) is applied to the hypotube. The coating is about 0.0005 inch thick.

Distal outer tube section 20 is a high density polyethylene tube having an outer diameter of about 0.0350 inch and an inner diameter of about 0.0294 inch, resulting in a distal outer tube wall thickness of about 0.0028 inch.

Proximal inner tube section 22 is a polyimide tube having an outer diameter of about 0.0220 inch and an inner diameter of about 0.0182 inch, resulting in a polyimide tube wall thickness of about 0.0019 inch.

Distal inner tube section 24 is a high density polyethylene tube having an outer diameter of about 0.0210 inch and an inner diameter of about 0.0162 inch, resulting in a wall thickness of about 0.0024 inch.

In this preferred embodiment, the distal end of inner bonding region 34 is spaced approximately 2 cm proximally from the proximal end of outer bonding region 32. In addition, inner bonding region 34 extends approximately 2 mm longitudinally along the catheter, outer bonding region 32 extends approximately 3.5 mm along the catheter, and that bonding region between distal end 20B of distal outer tube section 20 and proximal waist section 14A of balloon 14 (designated as bonding region 38) is approximately 3 mm in length.

This example of the preferred embodiment corresponds to a catheter with a balloon size of 2.0 mm, 2.5 mm or a 3.0 mm. The balloon size corresponds to the inflated diameter of the balloon 14 under an inflation pressure of approximately 6 atmospheres. The hypotube is approximately 39.75 inches long and the high density polyethylene distal outer tube section is approximately 13.5 inches long. The proximal polyimide inner tube section is approximately 39.25 inches long and the distal high density polyethylene inner tube section is approximately 15.8 inches long. The overall length of the catheter is approximately 55 inches.

This preferred embodiment of the catheter 10 of the present invention is intended for use in conjunction with a guide wire 21 having an outer diameter of about 0.014 inch. Such a guide wire is preferably about 69 inches in length.

As mentioned above, the use of high density polyethylene for the distal inner tube section 22 makes it more flexible than the polyimide proximal inner tube section 24. The reduction in inner and outer diameters of the distal inner tube section 24 relative to the proximal inner tube section 22 also permits enhanced flexibility thereof. In addition, establishing the joint (bonding region 34) between the polyimide proximal inner tube section 22 and polyethylene distal inner tube section 24 proximally of the distal end 18B of the hypotube 18 further enhances the distal flexibility of catheter 10, since the stiffer polyimide proximal inner tube section 22 does not project distally beyond the hypotube 18.

Although the present invention has been described with reference to preferred embodiments, workers skilled in the art will recognize changes may be made in form and detail without departing from the spirit of the scope of the invention. For example, materials other than those specifically mentioned yet having the same relative characteristics will work. Also, for use with balloons having other intended inflated profiles, different outer and inner diameter dimensions and lengths are possible for the various tube sections of the catheter.

WHAT IS CLAIMED IS:

1. A dilatation catheter comprising:
   an inner tube including a proximal inner tube section formed from a thin wall polymer tube and a distal inner tube section formed from a thin wall polymer tube connected together at an inner tube bonding region and having a guide wire lumen extending therethrough, with the distal inner tube section being more flexible than the proximal inner tube section;
   an outer tube positioned over the inner tube to define an inflation lumen between the inner tube and the outer tube, the outer tube having a proximal outer tube section formed from a thin wall metal tube and a distal outer tube section formed from a thin wall polymer tube connected together at an outer tube bonding region which is spaced distally from the inner tube bonding region, with the distal outer tube section being more flexible than the proximal outer tube section; and
   a balloon having a proximal portion connected to a distal end of the distal outer tube section and having a distal portion connected to a distal end of the distal inner tube section.

2. The dilatation catheter of claim 1 wherein the proximal outer tube section is a stainless steel hypotube.

3. The dilatation catheter of claim 1 wherein the proximal inner tube section is formed from a polyimide tube and the distal inner tube section is formed from a high density polyethylene tube.

4. The dilatation catheter of claim 1 wherein the distal outer tube section is formed from a high density polyethylene tube.

5. The dilatation catheter of claim 1 wherein the outer tube bonding region is spaced approximately 2 cm distally from the inner tube bonding region.

6. The dilatation catheter of claim 1 wherein the balloon is formed from a polyolefin copolymer material.

7. The dilatation catheter of claim 1 wherein the balloon is formed from a polyimide material.

8. The dilatation catheter of claim 1 wherein the inner tube bonding region is approximately 2 mm long.

9. The dilatation catheter of claim 1 wherein the outer tube bonding region is approximately 3.5 mm long.

10. The dilatation catheter of claim 1 wherein the outer tube has a lubricious material as at least a portion of its outer surface.

11. The dilatation catheter of claim 10 wherein the lubricious material is hydrophobic.

12. The dilatation catheter of claim 11 wherein the hydrophobic lubricious material is a polytetrafluoroethylene coating.

13. The dilatation catheter of claim 10 wherein the lubricious material is hydrophilic.

14. The dilatation catheter of claim 13 wherein the hydrophilic lubricious material is a polyacrylamide polyurethane substrate.

15. The dilatation catheter of claim 1 wherein the inner tube has a lubricious material as at least a portion of its inner surface.

16. The dilatation catheter of claim 15 wherein the lubricious material is hydrophobic.

17. The dilatation catheter of claim 16 wherein the hydrophobic lubricious material is a polytetrafluoroethylene coating.

18. The dilatation catheter of claim 16 wherein the hydrophobic lubricious material is a polyimidepolytetrafluoroethylene composite.

19. The dilatation catheter of claim 16 wherein the hydrophobic lubricious material is a polydimethylsiloxane coating.

20. The dilatation catheter of claim 15 wherein the lubricious material is hydrophilic.

21. The dilatation of claim 20 wherein the hydrophilic lubricious material is a polyacrylamide polyurethane substrate.

22. The dilatation catheter of claim 1 wherein the proximal tube sections are relatively long compared to their respective distal tube sections, wherein the guide wire lumen is reduced in diameter in the distal inner tube section, and wherein the longitudinal spacing between the proximal inner tube bonding region and the distal outer tube bonding region is relatively small whereby the length of the guide wire lumen defined by the distal inner tube section is relatively short.

23. The dilatation catheter of claim 1 wherein the outer tube has a maximum outer diameter of 0.0405 inch.

* * * * *